(12) United States Patent
Bae (10) Patent No.: US 11,775,067 B2
(45) Date of Patent: Oct. 3, 2023

(54) IMAGE DISPLAY DEVICE AND BIO-SIGNAL DETECTING METHOD USING THE SAME

(71) Applicant: LG DISPLAY CO., LTD., Seoul (KR)

(72) Inventor: Jungtae Bae, Goyang-si (KR)

(73) Assignee: LG DISPLAY CO., LTD., Seoul (KR)

( * ) Notice: Subject to any disclaimer, the term of this patent is extended or adjusted under 35 U.S.C. 154(b) by 0 days.

(21) Appl. No.: 17/555,783

(22) Filed: Dec. 20, 2021

(65) Prior Publication Data

US 2022/0206577 A1 Jun. 30, 2022

(30) Foreign Application Priority Data

Dec. 31, 2020 (KR) ........................ 10-2020-0188788

(51) Int. Cl.
| | |
|---|---|
| *G06V 40/13* | (2022.01) |
| *G06F 3/01* | (2006.01) |
| *G06F 3/041* | (2006.01) |
| *A61B 5/25* | (2021.01) |
| *G06F 3/042* | (2006.01) |

(52) U.S. Cl.
CPC ................ *G06F 3/015* (2013.01); *A61B 5/25* (2021.01); *G06F 3/0416* (2013.01); *G06F 3/0421* (2013.01); *G06V 40/1318* (2022.01)

(58) Field of Classification Search
CPC ...... G06F 3/015; G06F 3/0416; G06F 3/0421; G06F 3/0412; G06F 3/042–0428; G06F 21/32; A61B 5/25; A61B 5/02438; A61B 5/02444; A61B 5/6898; A61B 5/117; A61B 5/0059; A61B 5/02416; A61B 5/02427; A61B 2562/0233; A61B 2562/046; A61B 5/024; A61B 5/02405; G06V 40/1318; G06V 40/13; H01L 27/3225; H01L 27/3227; H01L 27/323; H01L 27/3234; H10K 59/131; H10K 59/00–771

See application file for complete search history.

(56) References Cited

U.S. PATENT DOCUMENTS

| | | | |
|---|---|---|---|
| 4,812,642 A * | 3/1989 | Hasegawa | ............. G06F 3/0421 345/82 |
| 2015/0268754 A1* | 9/2015 | Chang | .................. G09G 3/3413 345/175 |
| 2017/0027488 A1* | 2/2017 | Enenkel | ................. A61B 5/443 |
| 2017/0097702 A1* | 4/2017 | Chang | ..................... H04N 1/10 |
| 2017/0220839 A1* | 8/2017 | Yang | ................... H01L 27/3234 |

(Continued)

FOREIGN PATENT DOCUMENTS

KR 10-1621661 B1 5/2016

*Primary Examiner* — Roberto W Flores
(74) *Attorney, Agent, or Firm* — POLSINELLI PC (57) ABSTRACT

An image display device includes a display panel having a plurality of pixels, and a photoresistor pattern formed in a non-light emitting area between the plurality of pixels; a panel driving controller to drive light-emission control lines of the display panel; and a bio-signal detector that detects an output voltage of the photoresistor pattern which resistance is variable based on light reflected from the target object, and detects a bio-signal of the target object based on the detected output voltage, thereby, detecting the bio-signal of the target object using the image display light from the display panel may allow efficiently detecting the bio-signal without a separate light source or light source operation circuit for detecting the bio-signal.

12 Claims, 4 Drawing Sheets

(56) References Cited

U.S. PATENT DOCUMENTS

| | | | |
|---|---|---|---|
| 2018/0005007 A1* | 1/2018 | Du | G09G 3/3225 |
| 2018/0068166 A1* | 3/2018 | Zeng | A61B 5/6898 |
| 2019/0099096 A1* | 4/2019 | Wang | A61B 5/02427 |
| 2021/0200973 A1* | 7/2021 | Huang | G06F 3/0443 |

* cited by examiner

IMAGE DISPLAY DEVICE AND BIO-SIGNAL DETECTING METHOD USING THE SAME

CROSS-REFERENCE TO RELATED APPLICATION

This application claims the priority of Korean Patent Application No. 10-2020-0188788 filed on Dec. 31, 2020, which is hereby incorporated by reference in its entirety for all purposes.

BACKGROUND

Field of the Disclosure

The present disclosure relates to an image display device. More specifically, the present disclosure relates to an image display device capable of detecting a bio-signal of a target object using image display light of a display panel, and a bio-signal detecting method using the same.

Description of the Background

As the information society develops, a demand for display devices to display images is increasing in various forms. In recent years, flat panel display devices such as a liquid crystal display device (LCD), a quantum dot display device (QLED), and an organic light-emitting display device (OLED) have been used.

These flat panel display devices include a touch based display device which may provide a touch-based input scheme that allows a user to input information or commands intuitively and conveniently, rather than a mechanical input scheme using, for example, buttons, a keyboard, and a mouse. In order for the flat panel display device to provide the touch-based input scheme, it has been necessary for the device to detect presence or absence of a touch on a touch panel thereof by the user's body or an object and accurately detect touch coordinates (touch position).

In addition to simple touch detection, the device is now capable of detecting, recognizing and utilizing biometric information or a bio-signal such as a fingerprint as user authentication information for online banking, product purchase, application purchase and download, etc. Further, the device performs a function for health management including a function of detecting bio-signals based on a heart rate, a pulse, respiration, etc.

Conventionally, the flat panel display devices used in mobile communication devices such as tables or smartphones, etc. have employed a proximity touch sensor of a large area structure including silicon germanium (SiGe) or silicon (Si) based photo-transistors as means for recognizing the bio-signal.

In an early stage when a bio-signal recognition function was applied, the proximity touch sensor to recognize the bio-signal was formed on a peripheral component around the display panel such as a casing or an assembly structure of a flat display device. However, a structure for recognizing the bio-signal in which the proximity touch sensor was formed in an image display area of the display panel was proposed later.

In one example, in order to form a proximity touch sensor in the image display area of the display panel, the proximity touch sensor is disposed between pixels that display an image, or a touch pad on which the proximity touch sensors are arranged is disposed on a front face of the image display area.

In the conventional bio-signal recognition panel implementation scheme as described above, in order to dispose the proximity touch sensors between the pixels of the display panel, a pixel arrangement and design structure must be changed, or the proximity touch sensors must replace a predetermined number of pixels. Accordingly, problems of image quality degradation and cost increase were inevitable. Further, the approach of stacking the touch pad on the front face of the image display area caused problems such as complicating a manufacturing process while lowering brightness characteristics of the image.

SUMMARY

Accordingly, the present disclosure is to provide an image display device capable of detecting a bio-signal of a target object using image display light of a display panel that displays an image, and to provide a bio-signal detecting method using the same.

More specifically, the disclosure is to provide an image display device in which a photoresistor pattern is arranged in a non-light emitting area between pixels, and a bio-signal can be detected by detecting reflected light from a target object using the photoresistor pattern of the non-light emitting area, and to provide a bio-signal detecting method using the same.

Further, the present disclosure is to provide an image display device that may detect a bio-signal of a target object touched a display panel using a control signal supplied to pixels so that the pixels display an image, and a bio-signal detecting method using the same.

The present disclosure is not limited to the above-mentioned. Other features and advantages according to the present disclosure that are not mentioned may be understood based on following descriptions, and may be more clearly understood based on aspects according to the present disclosure. Further, it will be easily understood that the purposes and advantages according to the present disclosure may be realized using means shown in the claims and combinations thereof.

A image display device having a photo-sensitivity according to an aspect of the present disclosure includes a display panel including a plurality of pixels, and a photoresistor pattern formed in a non-light emitting area between adjacent pixels among the plurality of pixels; a panel driving controller to drive light-emission control lines of the display panel; and a bio-signal detector that detects an output voltage of the photoresistor pattern which resistance is variable based on light reflected from the target object, and detects a bio-signal of the target object based on the detected output voltage.

The photoresistor pattern is formed in a predefined bio-signal detecting area of the display panel, and is formed in a line shape extending in a vertical or horizontal direction and corresponding to the non-light emitting area between adjacent pixels among the plurality of pixels, or is arranged in a line shape curved in the vertical and horizontal directions.

Accordingly, the bio-signal detector may supply a DC driving voltage to the photoresistor pattern in real time, and, in response to at least one light-emission control signal among light-emission control signals respectively applied to the light-emission control lines, and may receive an output voltage from the photoresistor pattern as a bio-signal detection voltage, and may analyze a magnitude of the received bio-signal detection voltage, and then extract and count the bio-signal based on the analysis result.

A bio-signal detecting method using the image display device according to the aspect of the present disclosure may use the bio-signal detector to detect the output voltage from the photoresistor pattern which resistance is variable based on intensity of the light reflected from the target object for an image display period, and then may detect the bio-signal of the target object based on the output volage. In this connection, the bio-signal detector may receive the output voltage from the photoresistor pattern as a bio-signal detection voltage, in response to the at least one light-emission control signal among the plurality of light-emission control signals respectively applied to the light-emission control lines of the display panel. Moreover, the bio-signal is extracted and counted based on the analyzing result of the magnitude of the received bio-signal detection voltage.

The image display device and the bio-signal detecting method using the same according to the aspects of the present disclosure may detect the bio-signal of the target object using the image display light of the display panel, thereby efficiently detecting the bio-signal without a separate light source or light source operation circuit for detecting the bio-signal.

In particular, the photoresistor pattern may extend in and along the non-light emitting area between the pixels to detect the light reflected from the target object. Thus, a variation in the manufacturing process of the display panel may be minimized, while the sensitivity to the reflected light from the target object may be increased.

Further, the device may detect the bio-signal of the target object by sharing the control signal supplied to each pixel in order to control the image display operation of each of the pixels. Thus, a bio-signal detection circuit structure may be simplified without additionally generating a control signal for detecting the bio-signal. Accordingly, the image display device according to the present disclosure may perform a low-cost and high-efficiency biometric detecting function.

Effects of the present disclosure are not limited to the above-mentioned effects, and other effects as not mentioned will be clearly understood by those skilled in the art from following descriptions.

BRIEF DESCRIPTION OF THE DRAWINGS

The accompanying drawings, which are included to provide a further understanding of the disclosure and are incorporated in and constitute a part of the present disclosure, illustrate aspects of the disclosure and together with the description serve to explain the principle of the disclosure.

In the drawings.

DETAILED DESCRIPTION

For simplicity and clarity of illustration, elements in the drawings are not necessarily drawn to scale. The same reference numbers in different drawings represent the same or similar elements, and as such perform similar functionality. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure. Examples of various aspects are illustrated and described further below. It will be understood that the description herein is not intended to limit the claims to the specific aspects described. On the contrary, it is intended to cover alternatives, modifications, and equivalents as may be included within the spirit and scope of the present disclosure as defined by the appended claims.

A shape, a size, a ratio, an angle, a number, etc. disclosed in the drawings for describing an aspects of the present disclosure are exemplary, and the present disclosure is not limited thereto. The same reference numerals refer to the same elements herein. Further, descriptions and details of well-known steps and elements are omitted for simplicity of the description. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

The terminology used herein is for the purpose of describing particular aspects only and is not intended to limit the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entirety of list of elements and may not modify the individual elements of the list. When referring to "C to D", this means C inclusive to D inclusive unless otherwise specified.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" or "beneath" a second element or layer, the first element may be disposed directly on or beneath the second element or may be disposed indirectly on or beneath the second element with a third element or layer being disposed between the first and second elements or layers. It will be understood that when an element or layer is referred to as being "connected to", or "coupled to" another element or layer, it may be directly on, connected to, or coupled to the other element or layer, or one or more intervening elements or layers may be present. In addition, it will also be understood that when an element or layer is referred to as being "between" two elements or layers, it may be the only element or layer between the two elements or layers, or one or more intervening elements or layers may also be present.

Further, as used herein, when a layer, film, region, plate, or the like is disposed "on" or "on a top" of another layer, film, region, plate, or the like, the former may directly contact the latter or still another layer, film, region, plate, or the like may be disposed between the former and the latter. As used herein, when a layer, film, region, plate, or the like is directly disposed "on" or "on a top" of another layer, film, region, plate, or the like, the former directly contacts the latter and still another layer, film, region, plate, or the like is not disposed between the former and the latter. Further, as used herein, when a layer, film, region, plate, or the like is disposed "below" or "under" another layer, film, region, plate, or the like, the former may directly contact the latter or still another layer, film, region, plate, or the like may be disposed between the former and the latter. As used herein, when a layer, film, region, plate, or the like is directly disposed "below" or "under" another layer, film, region, plate, or the like, the former directly contacts the latter and still another layer, film, region, plate, or the like is not disposed between the former and the latter.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In one example, when a certain aspect may be implemented differently, a function or operation specified in a specific block may occur in a sequence different from that specified in a flowchart. For example, two consecutive blocks may actually be executed at the same time. Depending on a related function or operation, the blocks may be executed in a reverse sequence.

In descriptions of temporal relationships, for example, temporal precedent relationships between two events such as "after", "subsequent to", "before", etc., another event may occur therebetween unless "directly after", "directly subsequent" or "directly before" is not indicated. The features of the various aspects of the present disclosure may be partially or entirely combined with each other, and may be technically associated with each other or operate with each other. The aspects may be implemented independently of each other and may be implemented together in an association relationship. Spatially relative terms, such as "beneath," "below," "lower," "under," "above," "upper," and the like, may be used herein for ease of explanation to describe one element or feature's relationship to another element or feature as illustrated in the figures. It will be understood that the spatially relative terms are intended to encompass different orientations of the device in use or in operation, in addition to the orientation depicted in the figures. For example, when the device in the drawings is turned over, elements described as "below" or "beneath" or "under" other elements or features would then be oriented "above" the other elements or features. Thus, the example terms "below" and "under" may encompass both an orientation of above and below. The device may be otherwise oriented for example, rotated 90 degrees or at other orientations, and the spatially relative descriptors used herein should be interpreted accordingly.

Hereinafter, an image display device capable of detecting a bio-signal according to an aspect of the present disclosure will be described in more detail with reference to the accompanying drawings.

An image display device to which a bio-signal detection structure according to an aspect of the present disclosure may be applied may include a liquid crystal display device, a quantum dot display device, and an organic light-emitting display device, etc. Hereinafter, one example in which the image display device to which a bio-signal detection structure according to an aspect of the present disclosure is applied is embodied as an organic light-emitting display device as a self-luminous device is applied will be described. However, the disclosure is not limited thereto.

Figure 1:
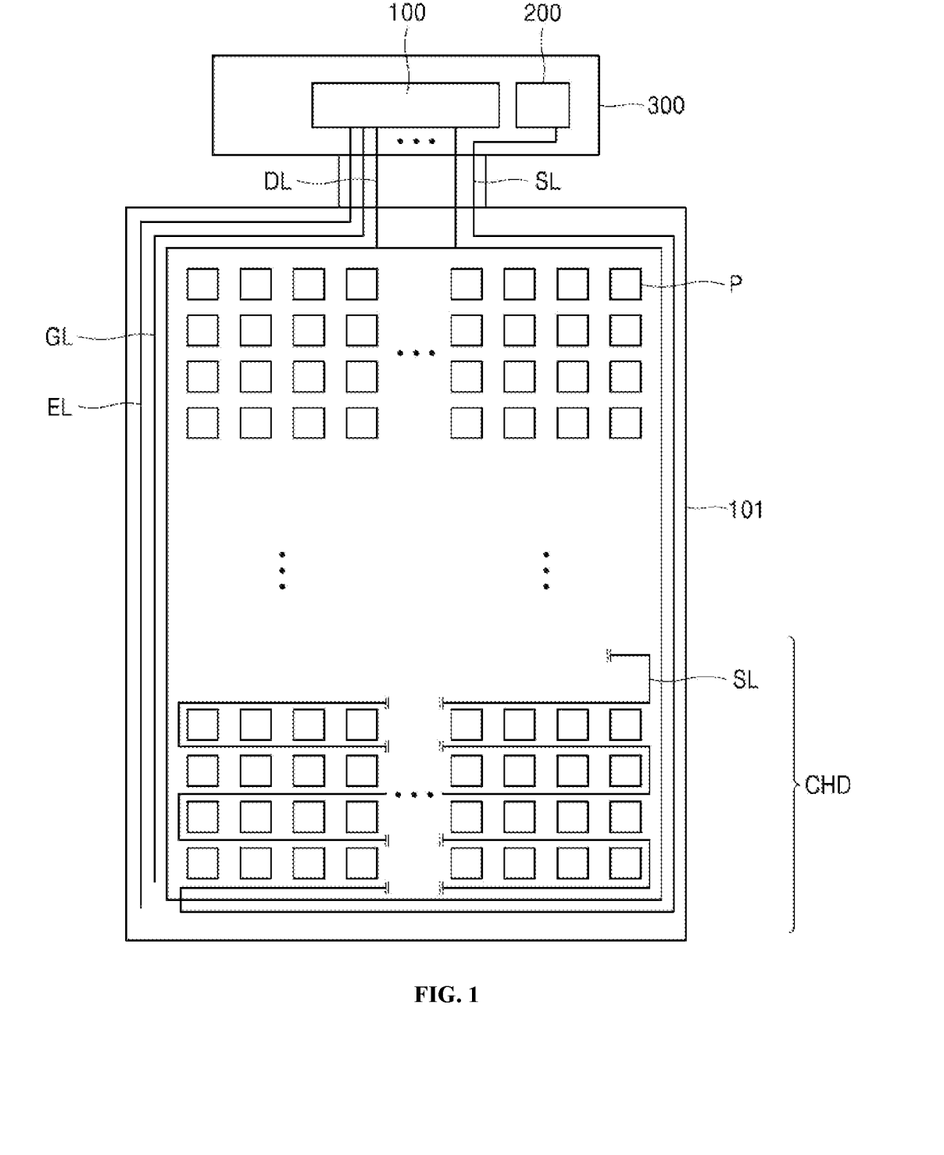
FIG. 1 is a configuration block diagram specifically showing an image display device according to an aspect of the present disclosure.
Figure 2:
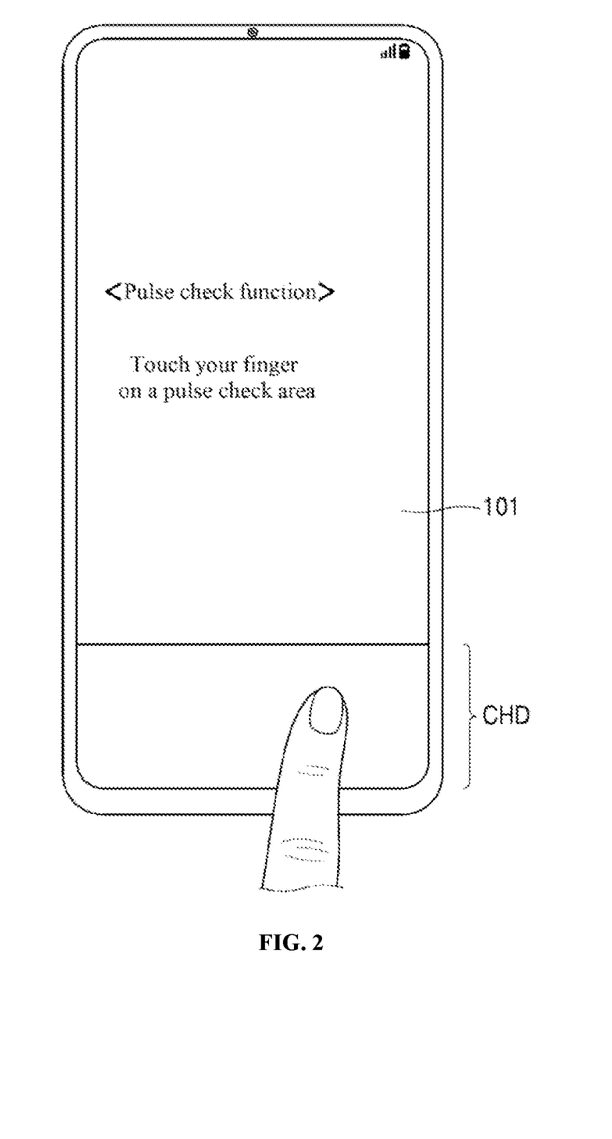
FIG. 2 is a diagram for illustrating a bio-signal detecting area and a bio-signal detecting method of and using the image display device shown in FIG. 1.

FIG. 1 is a configuration block diagram specifically showing an image display device according to an aspect of the present disclosure. FIG. 2 is a diagram for illustrating a bio-signal detecting area and a bio-signal detecting method of and using the image display device shown in FIG. 1.

An organic light-emitting display device shown in FIG. 1 has a display panel 101 on which a plurality of pixels P are disposed, a panel driving controller 100 to control a light-emission control line EL, and gate and data lines GL and DL of the display panel 101, and a bio-signal detector 200 that detects a bio-signal using a photoresistor pattern SL of the display panel 101.

In the display panel 101, a plurality of gate lines GL and a plurality of light-emission control lines EL intersect a plurality of data lines DL. Moreover, each pixel P is connected to at least one gate line GL, at least one light-emission control line EL, and at least one data line DL and is disposed at an intersection area therebetween.

Each pixel P receives a scan signal from the panel driving controller 100 through the gate line GL and receives a data voltage therefrom through the data line DL. Moreover, each pixel P receives a light-emission control signal through the light-emission control line EL, and receives high-potential and low-potential powers through separate power supply lines.

Each pixel P includes an organic light emitting element and a pixel circuit independently driving the organic light emitting element. The pixel circuit of each pixel P may be configured to include at least one switching transistor and a storage capacitor. Each pixel circuit charges a data voltage from the data line DL into the storage capacitor, and causes a current corresponding to the charged data voltage to flow in the organic light emitting element, such that the organic light emitting element may maintain a light-emitting state for a predefined frame period.

Referring to FIG. 2 together with FIG. 1, a bio-signal detecting area CHD may be defined in the display panel 101. In the bio-signal detecting area CHD, at least one photoresistor pattern SL may be arranged along a non-light emitting area between the pixels P.

The bio-signal to be detected may include a heart rate signal, or a pulse signal. For the heart rate or pulse detection, the light reflected from the target object may be received by the photoresistor pattern SL. In this connection, a variable resistance characteristic of the photoresistor pattern SL whose resistance value varies according to a change in a blood flow of the target object and thus a change in an amount of light may be used.

The bio-signal detecting area CHD in which at least one photoresistor pattern SL is arranged may be defined in a front face of the display panel 101, and may be defined as a predefined partial block area. Hereinafter, for convenience of description, an example in which the bio-signal detecting area CHD is defined in a lower ¼ area of the display panel 101 will be described.

At least one photoresistor pattern SL arranged in the bio-signal detecting area CHD may extend in a non-light emitting area between the pixels P and in a vertical or horizontal direction and/or may be bent between extensions in the vertical and horizontal directions. This photoresistor pattern SL has one end connected to the bio-signal detector 200 to receive a DC driving voltage from the bio-signal detector 200, and the opposite end connected in parallel to a low-potential voltage source (e.g., VSS) and the bio-signal detector. 200 is connected.

An input/output voltage of the photoresistor pattern SL corresponds to the DC driving voltage applied from the bio-signal detector 200. However, when a human body of the subject comes into contact with the bio-signal detecting area CHD, a resistance of the pattern SL is variable due to light reflected from the target object. Thus, a magnitude of the output voltage from the pattern SL may be variable, and may be equivalent to a resistance heat.

The panel driving controller 100 may be connected to a microprocessor, a mobile processor, and an application processor.

The panel driving controller 100 sequentially supplies a scan signal to the plurality of gate lines GL to allow the pixel circuits of the pixels P respectively connected to the gate lines GL to sequentially operate. In addition, the panel driving controller 100 sequentially supplies the light-emission control signal to the light-emission control lines EL to control the organic light emitting element of each pixel P to emit light according to the data voltage.

Further, the panel driving controller 100 aligns image data from an external system according to operation frequency and resolution characteristics of the display panel 101, and converts the image data into an analog data voltage on a horizontal line basis. Moreover, the panel driving controller 100 supplies the analog data voltage corresponding to every horizontal line to each data line DL in a synchronized manner with a scan signal input timing of each gate line GL.

Figure 3:
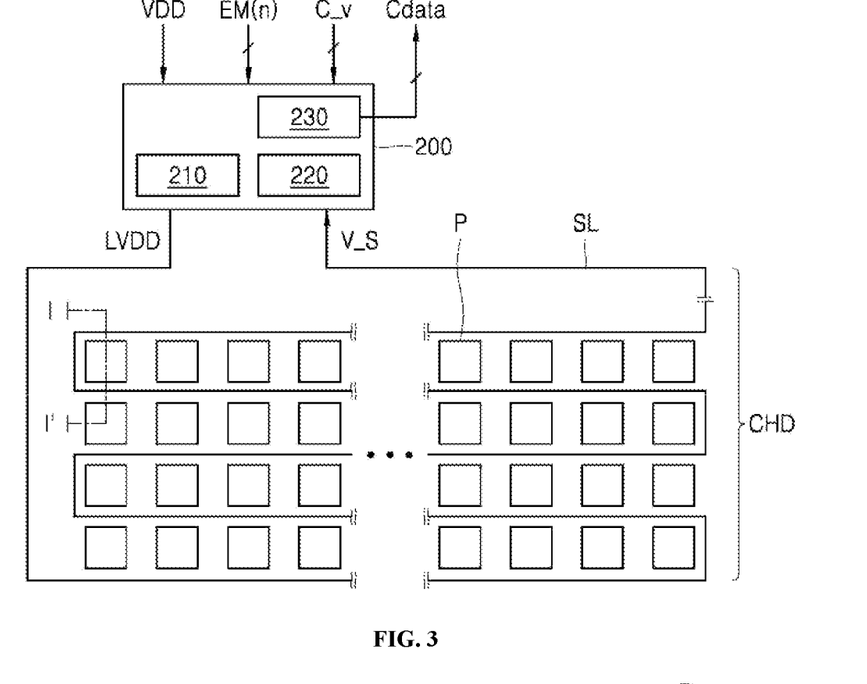
FIG. 3 is a block diagram specifically showing an arrangement structure of a photoresistor pattern as shown in FIG. 1 and a structure of a bio-signal detector as shown in FIG. 1.

FIG. 3 is a block diagram specifically showing an arrangement structure of a photoresistor pattern as shown in FIG. 1 and a structure of a bio-signal detector as shown in FIG. 1.

Referring to FIG. 3, the photoresistor pattern SL may be formed in a line shape that extends in the vertical and horizontal directions and in and along the non-light emitting area between the pixels P and is bent between the extensions in the vertical and horizontal directions.

One end of the photoresistor pattern SL is connected to the bio-signal detector 200 to receive a DC driving voltage LVDD maintained at a predefined voltage level from the bio-signal detector 200. The opposite end of the photoresistor pattern SL may be branched into two lines which may be connected to the bio-signal detector 200, and a low-potential voltage source (for example, VSS) through a resistor, respectively.

The magnitude of the input/output voltage of the photoresistor pattern SL corresponds to the magnitude of the DC driving voltage LVDD applied from the bio-signal detector 200. However, when the target object comes into contact with the bio-signal detecting area CHD, the resistance of the photoresistor pattern SL varies according to the intensity of light reflected from the target object and then incident to the photoresistor pattern SL. Therefore, when the target object touches the area CHD, the output voltage of the photoresistor pattern SL varies according to the intensity of the reflected light.

The bio-signal detector 200 reduces a high-potential voltage of a high-potential voltage source VDD to the DC driving voltage LVDD having a predefined voltage level and supplies the LVDD to at least one photoresistor pattern SL.

The bio-signal detector 200 may be connected in a parallel manner with the at least one photoresistor pattern SL while being disposed between and connected to a DC driving voltage LVDD supply terminal and a low-potential voltage source (for example, VSS) terminal. Accordingly, the bio-signal detector 200 supplies the DC driving voltage LVDD to the at least one photoresistor pattern SL and receives the output voltage output from the at least one photoresistor pattern SL as the bio-signal detection voltage V_S.

The bio-signal detector 200 may detect the bio-signal only by detecting the output voltage of the photoresistor pattern SL whose resistance varies based on the reflected light. The output voltage of the photoresistor pattern SL should be detected by the bio-signal detector 200 for a period when each pixel P of the display panel 101 displays an image.

To this end, the bio-signal detector 200 shares and receives at least one light-emission control signal among a plurality of light-emission control signals EM(n) respectively transmitted from the panel driving controller 100 to the plurality of light-emission control lines EL. Moreover, the bio-signal detector 200 supplies the DC driving voltage LVDD to the photoresistor pattern SL in real time, and detect the output voltage from the photoresistor pattern SL whenever at least one of the plurality of light-emission control signals EM(n) is inputted thereto. In this connection, the bio-signal detector 200 receives the output voltage output from the photoresistor pattern SL as the bio-signal detection voltage V_S, and analyzes the magnitude of the voltage and extracts and counts the bio-signal based on the analysis result.

A structure of the bio-signal detector 200 for extracting and counting the bio-signal includes a voltage converter 210, am output voltage detector 220, and a bio-signal analyzer 230.

The voltage converter 210 converts the high-potential voltage of the high-potential voltage source VDD into the DC driving voltage LVDD of the predefined voltage magnitude and supplies the LVDD to at least one photoresistor pattern SL. The voltage converter 210 may include at least one amplifier, a comparator, an AD converter, a DC converter, etc.

The output voltage detector 220 may share and receive at least one light-emission control signal among the plurality of light-emission control signals EM(n) respectively applied to the plurality of light-emission control lines EL, and receives the output voltage from the at least one photoresistor pattern SL as the bio-signal detection voltage V_S in response to the reception of the at least one light-emission control signal. In this connection, the output voltage detector 220 may use the at least one light-emission control signal as a switching signal.

The bio-signal analyzer 230 may compare the magnitude of the voltage of the bio-signal detection voltage V_S detected every at least one light-emission control signal input period with a predefined bio-signal detection reference, and count the bio-signal based on the comparison result. Alternatively, the bio-signal analyzer 230 may convert the bio-signal detection voltage V_S in an analog to digital conversion manner and compare the converted digital value with the bio-signal detection reference and count the bio-signal based on the comparison result. Thereafter, the bio-signal analyzer 230 may provide the counted bio-signal detection data Cdata to an external system or the panel driving controller 100.

Figure 4:
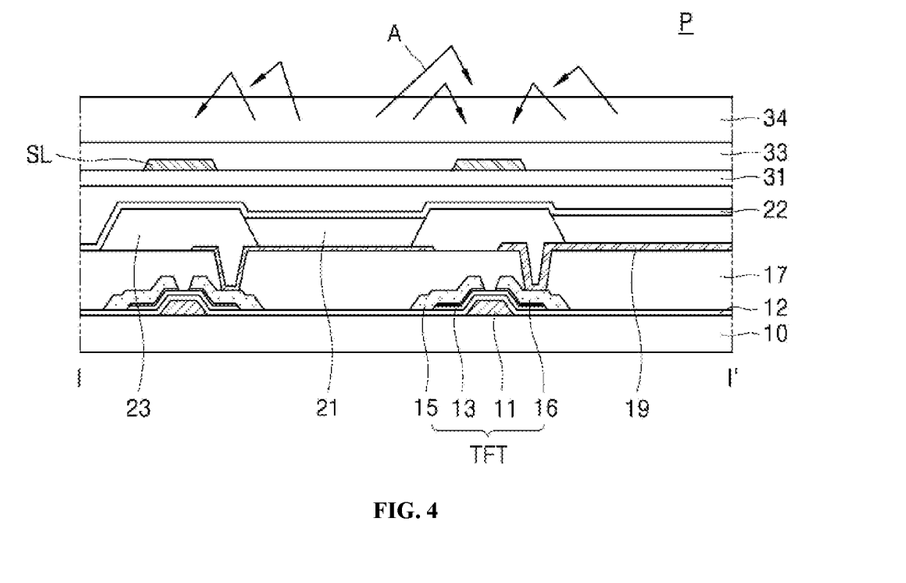
FIG. 4 is a cross-sectional view taken along a line I-I' shown in FIG. 3.

FIG. 4 is a cross-sectional view taken along a line I-I' shown in FIG. 3.

Referring to FIG. 3 and FIG. 4, each pixel P provided in the display panel 101 includes an organic light-emissive layer 21 constituting the organic light-emissive diode, and at least one switching transistor TFT for controlling a current of the organic light-emissive layer 21.

Each switching transistor TFT is formed in the non-display area of the substrate 10 and may include a gate electrode 11, a gate insulating film 12, source/drain electrodes 15 and 16, a semiconductor layer 13, an ohmic contact layer, and a protective film 17.

A first electrode 19 constituting the organic light-emissive diode is connected to each switching transistor TFT via a contact hole defined in the protective film 17 covering each switching transistor TFT, so that the organic light-emissive layer 21 is electrically connected to the switching transistor TFT. A second electrode 22 is formed over an entire face of the substrate 10 including the organic light-emissive layer 21. Thus, the first electrode 19, the organic light-emissive layer 21 and the second electrode 22 constitute one organic light-emissive diode.

In this connection, a pixel defining layer such as a spacer 23 or a bank may be formed as a partitioning wall in the non-display area, that is, the non-light emitting area as a peripheral area of each pixel P surrounding each pixel P. The spacer 23 is formed a non-light emitting area except for the light emitting area in which the organic light-emissive diode emits light. The spacer 23 is made of an insulating material such as silicon oxide (SiOx), silicon nitride (SiNx), photo acryl, or benzocyclobutene (BCB).

The photoresistor pattern SL may be formed in a form of a line patterned along the non-light emitting area corresponding to the spacer 23 between the pixels P. To this end, the photoresistor pattern SL may be formed to overlap the spacer 23 and on the spacer 23 between the pixels P.

The photoresistor pattern SL may be formed on the spacer 23 and may be spaced from by a regular distance from the spacer 23 and may have a smaller width and a smaller thickness than those of the spacer 23, and thus may receive the light from the organic light-emissive diode reflected from the target object. The photoresistor pattern SL may be made of a conductive material such as cadmium sulfide (CdS) whose resistance value varies according to the intensity of the received light.

Figure 5:
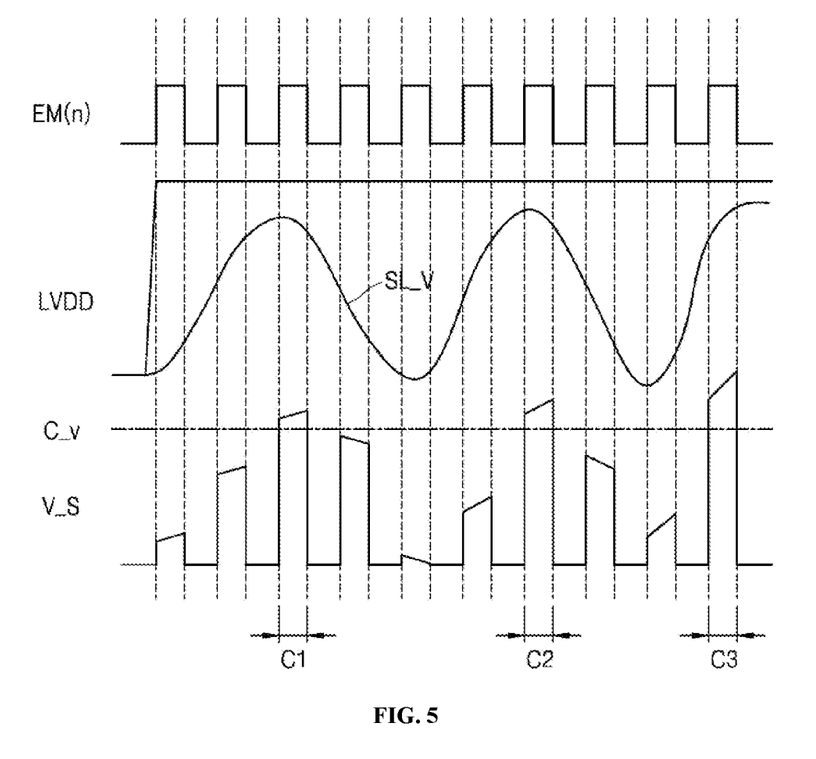
FIG. 5 is a control signal and a detection signal timing diagram for illustrating a bio-signal detection method using the bio-signal detector as shown in FIG. 3.

FIG. 5 is a control signal and a detection signal timing diagram for illustrating a bio-signal detection method using the bio-signal detector as shown in FIG. 3.

Referring to FIG. 5 together with FIG. 3, the voltage converter 210 of the bio-signal detector 200 converts the external high-potential voltage into a DC driving voltage LVDD of the predefined voltage magnitude, and supplies the LVDD to the photoresistor pattern SL in real time while the display panel 101 is operating.

The input/output voltage SL_v of the photoresistor pattern SL corresponds to the DC driving voltage LVDD. However, when the target object comes into contact with the bio-signal detecting area CHD, the resistance of the pattern SL is variable according to the intensity of light A reflected from the target object and then received by the pattern SL. Thus, the output voltage SL_v thereof varies according to the change in the blood flow of the target object and thus the intensity of the reflected light A.

The output voltage detector 220 of the bio-signal detector 200 shares and receive at least one light-emission control signal among the plurality of light-emission control signals EM(n). Moreover, in response to the reception of the at least one light-emission control signal, the output voltage detector 220 of the bio-signal detector 200 receives the output voltage SL_v output from the at least one photoresistor pattern SL as the bio-signal detection voltage V_S.

In this connection, the output voltage detector 220 may use the at least one light-emission control signal as a switching signal. Thus, for each period in which at least one light-emission control signal EM n having a turn-on level is input to the output voltage detector 220, the output voltage detector 220 may detect the output voltage SL_v from the at least one photoresistor pattern SL.

The bio-signal analyzer 230 of the bio-signal detector 200 compares the magnitude of the voltage of the bio-signal detection voltage V_S detected every at least one light-emission control signal input period with the predefined bio-signal detection reference C_v. In this connection, the bio-signal analyzer 230 uses at least one amplifier and comparator circuit to compare the magnitude of the voltage of the bio-signal detection voltage V_S and the bio-signal detection reference C_v with each other, and then counts (C1, C2, C3) the bio-signal according to the comparison result.

Alternatively, the bio-signal analyzer 230 may convert the bio-signal detection voltage V_S in the AD conversion manner, and compare the converted digital value with the bio-signal detection reference C_v, and count (C1, C2, C3) the bio-signals according to the comparison result. Thus, the counted bio-signal detection data Cdata generated from the bio-signal analyzer 230 may be provided to an external system or the panel driving controller 100.

As described above, the image display device and the bio-signal detecting method using the same according to the aspects of the present disclosure may detect the bio-signal of the target object using the image display light of the display panel 101, thereby efficiently detecting the bio-signal without a separate light source or a separate light source driving circuit for detecting the bio-signal.

In particular, the photoresistor pattern SL extending in the non-light emitting area between the pixels P may be used to detect the reflected light from the target object. Thus, a variation in the manufacturing process of the display panel 101 may be minimized, while the sensitivity to the reflected light from the target object may be increased.

Further, the device may detect the bio-signal of the target object by sharing the control signal supplied to each pixel in order to control the image display operation of each of the pixels P. Thus, a bio-signal detection circuit structure may be simplified without additionally generating a control signal for detecting the bio-signal. Accordingly, the image display device according to the present disclosure may perform a low-cost and high-efficiency biometric detecting function.

Although the aspects of the present disclosure have been described in more detail with reference to the accompanying drawings, the present disclosure is not necessarily limited to these aspects. The present disclosure may be implemented in various modified manners within the scope not departing from the technical idea of the present disclosure. Accordingly, the aspects disclosed in the present disclosure are not intended to limit the technical idea of the present disclosure, but to describe the present disclosure. the scope of the technical idea of the present disclosure is not limited by the aspects. Therefore, it should be understood that the aspects as described above are illustrative and non-limiting in all respects. The scope of protection of the present disclosure should be interpreted by the claims, and all technical ideas within the scope of the present disclosure should be interpreted as being included in the scope of the present disclosure.

What is claimed is:

1. An image display device comprising:
a display panel including a plurality of pixels and a photoresistor pattern formed in a non-light emitting area between adjacent pixels among the plurality of pixels;
a panel driving controller configured to drive gate and data lines, and light-emission control lines of the display panel; and
a bio-signal detector configured to detect an output voltage of the photoresistor pattern during an image display operation and detect a bio-signal of the target object, based on the detected output voltage,
wherein a resistance value of the photoresistor pattern varies based on intensity of light reflected from a target object during the image display operation, and
wherein the photoresistor pattern is formed in a single continuous line shape that is variously bent in the vertical and horizontal directions along the non-light emitting area among the plurality of pixels, and
wherein the photoresistor pattern is separated with and completely overlaps with a switching transistor between adjacent pixels among the plurality of pixels.

2. The device of claim 1, wherein the photoresistor pattern is formed in a bio-signal detecting area of the display panel, and
wherein the photoresistor pattern is arranged in a vertical or horizontal direction corresponding to the non-light emitting area between adjacent pixels among the plurality of pixels, or is arranged in a curved line shape in the vertical and horizontal directions.

3. The device of claim 2, wherein one end of the photoresistor pattern is connected to the bio-signal detector such the pattern receives a direct current (DC) driving voltage maintained at a predefined voltage magnitude from the bio-signal detector, and
wherein another end of the photoresistor pattern is branched into two lines which are connected to the bio-signal detector and a low-potential voltage source through a resistor.

4. The device of claim 2, wherein the photoresistor pattern is formed in a form of a line patterned along the non-light emitting area such that the photoresistor pattern overlaps with a spacer between adjacent pixels among the plurality of pixels.

5. The device of claim 2, wherein the photoresistor pattern is formed on the spacer between adjacent pixels among the plurality of pixels and is vertically spaced apart from the spacer by a constant vertical spacing, and
wherein the photoresistor pattern has a width and a thickness smaller than a width and a thickness of the spacer such that the photoresistor pattern receives the light reflected from the target object.

6. The device of claim 2, wherein the photoresistor pattern is formed of a conductive material which resistance value varies based on the intensity of the light reflected from the target object and incident thereto when the target object comes into contact with the bio-signal detecting area.

7. The device of claim 1, wherein the bio-signal detector is configured to:
supply a DC driving voltage to the photoresistor pattern in real time in response to one light-emission control signal among light-emission control signals applied to the light-emission control lines,
receive the output voltage from the photoresistor pattern as a bio-signal detection voltage; and
analyze a magnitude of the bio-signal detection voltage, and extract and count the bio-signal based on the analyzed magnitude.

8. The device of claim 1, wherein the bio-signal detector includes:
a voltage converter configured to convert a high-potential voltage into a DC driving voltage having a predefined voltage magnitude and supply the DC driving voltage to the photoresistor pattern;
an output voltage detector configured to detect the output voltage from the photoresistor pattern as a bio-signal detection voltage, using at least one light-emission control signal among light-emission control signals respectively applied to the light-emission control lines as a switching signal; and
a bio-signal analyzer configured to compare a magnitude of the bio-signal detection voltage with a predefined bio-signal detection reference, and to count the bio-signal based on the comparing result, and to provide the counted bio-signal to an external system or the panel driving controller.

9. A bio-signal detecting method using an image display device including a display panel including a plurality of pixels and a photoresistor pattern formed in a non-light emitting area between adjacent pixels among the plurality of pixels, and a panel driving controller for driving light-emission control lines of the display panel, the method comprising:
supplying a DC driving voltage to the photoresistor pattern in real time;
detecting, by a bio-signal detector, an output voltage of the photoresistor pattern during an image display operation, wherein a resistance value of the photoresistor pattern varies based on intensity of light reflected from a target object during the image display operation; and
detecting a bio-signal of the target object, based on the detected output voltage,
wherein the photoresistor pattern is formed in a single continuous line shape that is variously bent in the vertical and horizontal directions along the non-light emitting area among the plurality of pixels, and
wherein the photoresistor pattern is separated with and completely overlaps with a switching transistor between adjacent pixels among the plurality of pixels.

10. The method of claim 9, wherein the detecting the bio-signal of the target object includes:
receiving the output voltage from the photoresistor pattern as a bio-signal detection voltage, in response to one light-emission control signal among the plurality of light-emission control signals respectively applied to the light-emission control lines of the display panel; and
analyzing a magnitude of the received bio-signal detection voltage, and extracting and counting the bio-signal based on the analyzing result.

11. The method of claim 9, wherein the detecting the bio-signal of the target object includes:

receiving the output voltage from the photoresistor pattern as a bio-signal detection voltage, wherein at least one light-emission control signal among a plurality of light-emission control signals respectively applied to the light-emission control lines of the display panel is used as a switching signal, comparing a magnitude of the bio-signal detection voltage with a predefined bio-signal detection reference;

counting the bio-signal based on the compared magnitude; and providing the counted bio-signal to an external system or the panel driving controller.

12. An image display device comprising:

a display panel including a plurality of pixels and a photoresistor pattern formed in a non-light emitting area between adjacent pixels among the plurality of pixels;

a panel driving controller configured to drive gate and data lines, and light-emission control lines of the display panel; and a bio-signal detector configured to detect an output voltage of the photoresistor pattern during an image display operation and detect a bio-signal of the target object, based on the detected output voltage, wherein a resistance value of the photoresistor pattern varies based on intensity of light reflected from a target object during the image display operation, wherein the photoresistor pattern is formed in a continuously line shape that is variously bent in the vertical and horizontal directions along the non-light emitting area among the plurality of pixels, wherein the photoresistor pattern is separated with and completely overlaps with a switching transistor between adjacent pixels among the plurality of pixels, wherein a magnitude of the input/output voltage of the photoresistor pattern corresponds to a direct current (DC) driving voltage applied from the bio-signal detector, and wherein, when the target object touches a bio-signal detecting area, the output voltage of the photoresistor pattern varies according to the intensity of light reflected from the target object.

* * * * *